United States Patent [19]

Kumakura

[11] Patent Number: 4,765,313
[45] Date of Patent: Aug. 23, 1988

[54] OBJECTIVE PART REPLACEABLE ENDOSCOPE TIP

[75] Inventor: Masahiro Kumakura, Zama, Japan

[73] Assignee: Olympus Optical Co., Ltd., Tokyo, Japan

[21] Appl. No.: 77,927

[22] Filed: Jul. 27, 1987

[30] Foreign Application Priority Data

Aug. 1, 1986 [JP] Japan ................ 61-181631

[51] Int. Cl.⁴ ............................................. A61B 1/00
[52] U.S. Cl. ........................................... 128/4; 128/6
[58] Field of Search ................ 128/3, 4, 5, 6, 7; 350/96.26

[56] References Cited

U.S. PATENT DOCUMENTS

| | | | |
|---|---|---|---|
| 4,569,333 | 2/1986 | Bel et al. | 128/4 |
| 4,660,982 | 4/1987 | Okada | 128/6 X |
| 4,685,450 | 8/1987 | Collins et al. | 128/4 |
| 4,706,653 | 11/1987 | Yamamoto | 128/4 |

FOREIGN PATENT DOCUMENTS

| | | |
|---|---|---|
| 31-158203 | 12/1956 | Japan . |
| 32-87704 | 12/1957 | Japan . |
| 35-59214 | 12/1960 | Japan . |
| 35-59215 | 12/1960 | Japan . |

*Primary Examiner*—William H. Grieb
*Attorney, Agent, or Firm*—Armstrong, Nikaido, Marmelstein & Kubovcik

[57] ABSTRACT

An endoscope tip is fittable with either (a) a first kind of objective part, having an objective optical system provided with a rotary adjusting mechanism or (b) a second kind of objective part having an objective optical system provided with no rotary adjusting mechanism. A non-rotary connecting mechanism is formed for the first kind of objective part and a rotary connecting mechanism is formed for the second kind of objective part so that the connecting mechanism may not loosen when there is a rotary adjustment of the objective in order to focus the same.

11 Claims, 4 Drawing Sheets

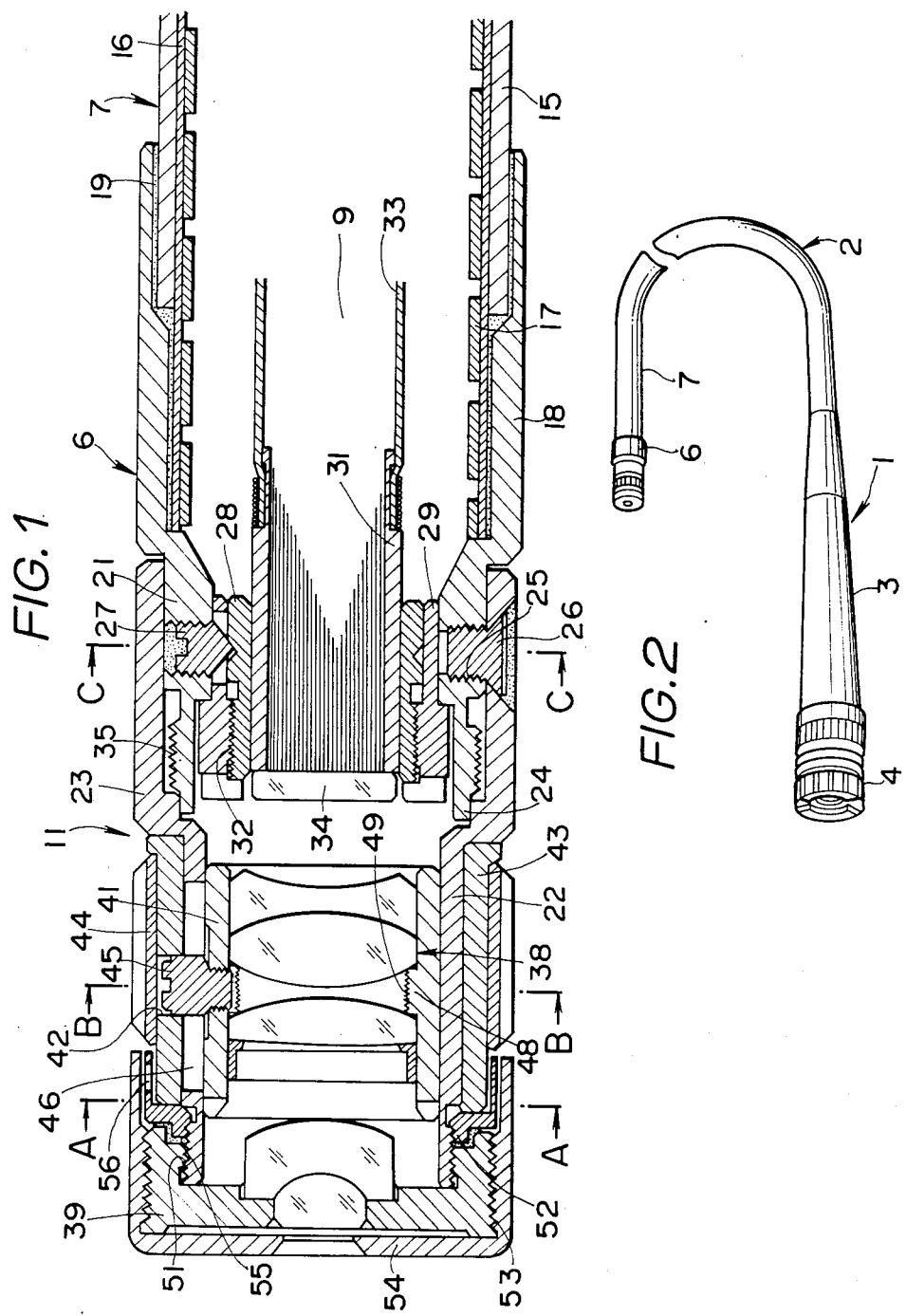

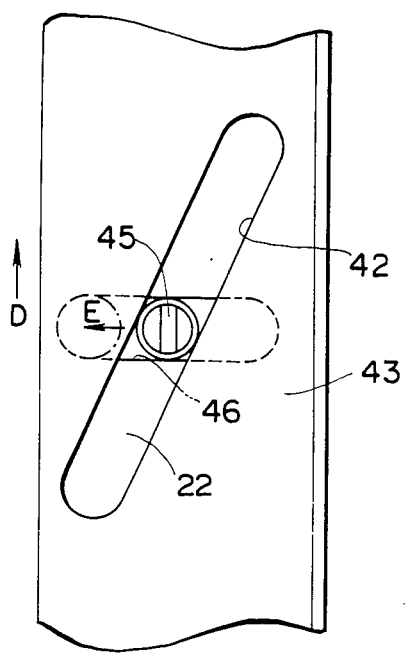
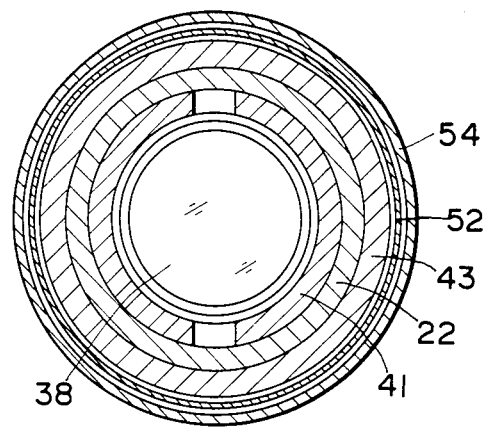
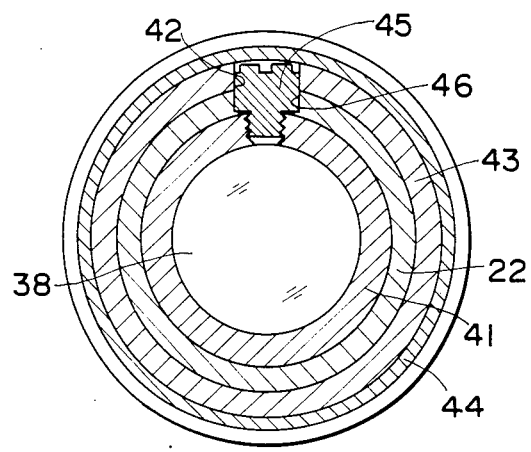

OBJECTIVE PART REPLACEABLE ENDOSCOPE TIP

BACKGROUND OF THE INVENTION

Field of the Invention and Related Art Statement

This invention relates to an objective part replaceable endoscope tip. The objective part is provided with an objective optical system in which the focus is adjustable by a rotating operation. The objective part of a fixed focus system can be selectively removably fitted.

Generally, in an endoscope, an objective part, in which an objective optical system is formed, and a soft part, forming a flexible insertable part, are integral. However, there is also an endoscope in which the objective part has a replaceable structures. In the endoscope having a replaceable objective part, objective parts of the three below mentioned types are selectively fitted:

(1) An objective part in which the focus is adjustable by rotating a focus ring by hand.

(2) An objective part to the tip of which a hood or a visual field converting adapter, which converts a visual field angle and visual field direction, can be removably fitted. (This objective part may be either a fixed focus system or an adjustable focus system.)

(3) An objective part of a fixed focus to the tip of which a visual field converting adapter, which converts a visual field angle and visual field direction, can not be removably fitted.

The prior art examples relating to the objective parts of the above mentioned three types are Japanese utility models laid open Nos. 158203/1981, 87704/1982, 59114/1985 and 59215/1985 by the present applicant.

The above mentioned prior art examples, which are frequently removably fitted, have been connected with a soft part by a rotary engagement of a screw mount by which they can be easily removably fitted.

However, one defect in the above mentioned type (1), is that at the time of the focus adjusting operation by rotating the objective part, torque will be applied to the screw mount part of the objective part, and thus the connection with the soft part will loosen. One defect in the above mentioned type (2), is that when the hood or visual field converting adapter, connected to the objective part, is to be disconnected, the connection will also loosen.

OBJECTS AND SUMMARY OF THE INVENTION

One object of the present invention is to provide an objective part replaceable endoscope tip in which the objective part, which can adjust the focus by a rotating operation, can be connected without loosening the connection by a rotating operation.

Another object of the present invention is to provide an objective part replaceable endoscope tip in which the objective part, which has no rotating operation mechanism for adjusting the focus, can be easily removably fitted by a rotary connection.

In the present invention, a non-rotary connecting part and a rotary connecting part are provided as a connecting means for different kinds of objective parts. The objective part has an adjusting mechanism which functions as a focus adjusting means by a rotating operation. The objective part is connected by means of a non-rotary connecting part. On the other hand, the objective part which has no adjusting mechanism is connected by means of a rotary connecting part. Thus, the objective part which has the adjusting mechanism may not have its connection to the endoscope tip loosened by the rotating operation. Also, the objective part which has no adjusting mechanism may be easily removably fitted by the rotary connection.

BRIEF DESCRIPTION OF THE DRAWINGS

FIGS. 1 to 10 relate to an embodiment of the present invention.

FIG. 1 is a sectioned view showing an endoscope tip of the embodiment fitted with a standard objective part.

FIG. 2 is a perspective view showing an entire endoscope in which the embodiment is formed.

FIG. 3 is a developed view showing a cam member forming a focus adjusting mechanism in FIG. 1.

FIG. 4 is a sectioned view on line A—A in FIG. 1.

FIG. 5 is a sectioned view on line B—B in FIG. 1.

FIG. 6 is a sectioned view on line C—C in FIG. 1.

FIG. 7 is a sectioned view showing a visual field angle converting optical adapter fittable to the front part of the standard objective part.

FIG. 8 is a front view of FIG. 7.

FIG. 9 is a sectioned view showing a high magnification objective part fittable to the embodiment by a rotating operation.

FIG. 10 is a front view of FIG. 9.

DETAILED DESCRIPTION OF THE PREFERRED EMBODIMENT

Figure 6:
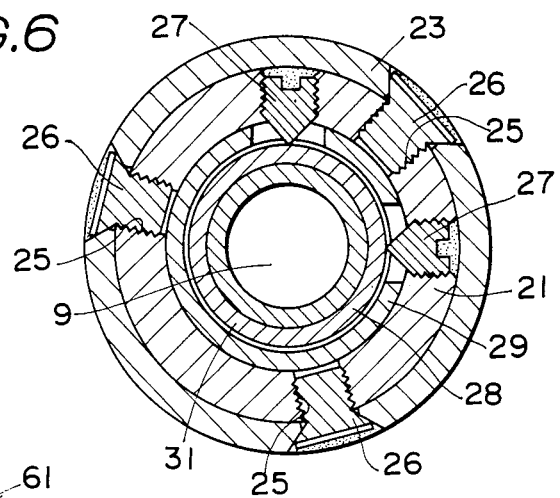

As shown in FIG. 2, an endoscope 1 of the embodiment of the present invention is formed comprising an elongated flexible insertable part 2. A thick holding part 3 is connected to the rear end side of the insertable part 3. An eyepiece part 4 is formed at the rear end of the holding part 3. An endoscope tip 6 (which shall be referred to merely as the tip 6 hereinafter) is formed at the front end of the insertable part 2. A curvable flexible soft part 7 is formed on the rear side adjacent to the tip 6.

As shown in FIG. 1, an image guide 9, which functions as an image transmission means, is inserted through the insertable part 2 so that an image formed on the front end surface of the image guide 9 may be transmitted to the rear end surface of the image guide 9. The transmitted image may be magnified and observed from the rear of the eyepiece part 4 through an eyepiece not illustrated. The image guide 9 is formed from a flexible fiber bundle.

A standard objective part 11 as a first kind of objective part shown in FIG. 1 can be removably fitted to the tip 6. A high magnification objective part 12 as a second kind of objective part shown in FIG. 9 can be removably fitted instead of the standard objective part 11.

The insertable part 2 has a jacket tube formed of a flexible soft tube 15. A thin-walled tube 16 formed of a net pipe or the like is internally fitted inside the soft tube 15. A spiral pipe 17 is internally fitted inside the tube 16.

The soft tube 15 and the tube 16 forming the insertable part 2 are internally fitted at the front ends in a substantially tubular tip member 18 forming the tip 6 and are secured with cement 19. Also, spiral pipe 17 is secured at the front end to the tip member 18 by brazing or the like. The outside diameter of the tip member 18 is made somewhat larger than the outside diameter of the soft tube 15 to define the fixed part.

The forward outside diameter of the tip member 18 is made steppedly smaller to form a front mouthpiece part 21. For example, a fitting ring part 23 on the rear side of a (standard objective part) body 22, forming the standard objective part 11, may be externally fitted to the front mouthpiece part 21. The outside diameter of the front mouthpiece part 21 and the inside diameter of the ring part 23 are made substantially equal to each other.

The front mouthpiece part 21 is made somewhat smaller in diameter at the front end to form a small diameter part 24. On the other hand, the part corresponding to the ring part 23 of the standard objective part 11 has a small inside diameter so as to be fittable to the small diameter part 24. The standard objective part 11 is fitted to the two parts of the front mouthpiece part 21 and the small diameter part 24 so that the axis in fitting the standard objective part 11 may be positively positioned and the optical axis may be prevented from being deflected.

The ring part 23 fitted in the two parts is positively fitted by flush fitting screws 26 respectively which are screwed into, for example, three screw holes 25. The screw holes 25 are made in the front mouthpiece part 21 of the tip member 18 through holes made in the ring part 23 (see FIG. 6) so that the standard objective part will not wobble.

For example, two screw holes are made in the front mouthpiece part 21 beside the screw holes 25. An image guide receiver 28, which is internally fitted inside the front mouthpiece part 21, is fixed with screws 27 screwed into the respective screw holes. The image guide receiver 28 is not fitted directly into the front mouthpiece part 21 but is fixed by fitting an image guide holder 29 between them.

That is to say, the image guide receiver 28 is secure with cement or the like on the outer periphery of an image guide mouthpiece 31 is fitted to the outer periphery of the front end of the image guide 9. The image guide holder 29, which is provided with a screw hole screwed with a male screw 32 formed on the front side of the outer peripheral surface of the image guide receiver 28, is screwed to the image guide receiver 28. The rear outer peripheral part of the image guide holder 29 is fitted into the front mouthpiece part 21. The screws 27 screwed into the respective screw holes pass through the holes of the image guide holder 29 and collide at the tips with recesses on the image guide receiver 28 to securely fix the image guide 9 to the image guide receiver 28. Thus, the image guide 9 receiving member is made of two bodies consisting of the image guide holder 29 and image guide receiver 28 so that the image guide 9 may be assembled from the eyepiece side.

The image guide 9 is coated with a protective tube 33 fixed at the front end to the mouthpiece 31 by winding a thread-like member. A glass plate 34 is provided for preventing dust or the like from being deposited inside the image guide 9. The glass plate 34 is secured to the front end surface of the image guide. A removably fitting male screw part 35 is formed adjacent to the rear part of the small diameter part 24 at the front end of the front mouthpiece part 21. The male screw part 35 forms a rotary connecting part which can fit a female screw part 36 of a high magnification objective part 12 shown in FIG. 9.

The standard objective part 11, which is fitted to the front mouthpiece part 21, contains an objective optical system 38 in which a focus adjusting mechanism is formed.

The objective optical system 38 consists of an objective front lens secured to a front frame 39 and an objective rear lens secured to a sliding ring 41.

The sliding ring 41 fits in a small diameter part which is made steppedly small from the body 22 and is made slidable. A cam member 43, in which a cam groove 42 is formed, is externally fitted on the outer periphery of the small diameter part. A focus ring 44, for a focus adjusting operation, is secured with cement or the like on the outer periphery of the cam member 43.

A cam pin 45 is provided to project on to the sliding ring 41. The cam pin 45 passes through a slot 46 formed in the small diameter part and is engaged at the top with the cam groove 42. Therefore, when the focus ring 44 is rotated, the cam groove 42 will be rotated together with the focus ring 44. Therefore, the position of the cam pin 45, engaged with the cam groove 42, will move forward and rearward in the direction of the optical axial of the objective optical system 38. The objective rear lens will move forward and rearward together with the cam pin 45 so that the focus may be adjusted. For example, in FIG. 3, if the cam member 43 is moved in the direction indicated by the arrow D (by the operation of rotating the focus ring 44), the sliding ring 41, provided with the projecting cam pin 45, will be moved in the direction E of the cam pin in the position indicated by the one-point chain line so that the focus can be adjusted.

The outside diameter of the top of the cam pin 45 engaged with the cam groove 42 is made small so that, even if the cam pin 45 is deformed at the top when it is screwed in, the deformed part will not adversely influence the cam groove 42 of the cam member 43.

A spacing projection 48 functions as a spacer and holds the respective lenses which form the objective rear lens in the sliding ring 41 at a predetermined spacing. The spacing projection 48 is provided on the inner peripheral surface of the sliding ring 41. The surface of the projection 48, except in the front and rear edge parts, has a spiral groove or rough surface to form a light shield 49 for preventing flares.

A focus ring 44 is knurled on the outer peripheral surface so as to be smoothly rotated without slipping.

A screw part 51 is formed on the outer periphery at the front end of the small diameter part of the body 22. A ring presser 52 and the front frame 39 are screwed to the screw part 51. A screw part 53 is also formed on the outer peripheral surface of the front frame 39 so that a hood 54 may be removably fitted by screwing.

The front frame 39 is connected to the body 22 by screwing and then further securing the frame 39 with cement 55 to strengthen the connection. The ring presser 52 is fitted between the front frame 39 and the body 22 to prevent the binder 55 from flowing in toward the cam member 43. The ring presser 52 is provided with a caulking hole 56 to be able to be strongly secured to the cam member 43 utilizing the caulking hole 56.

Figure 8:
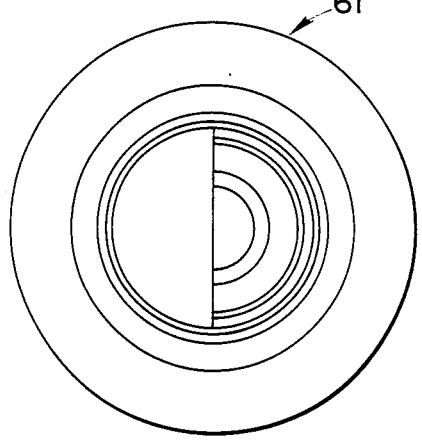
Figure 7:
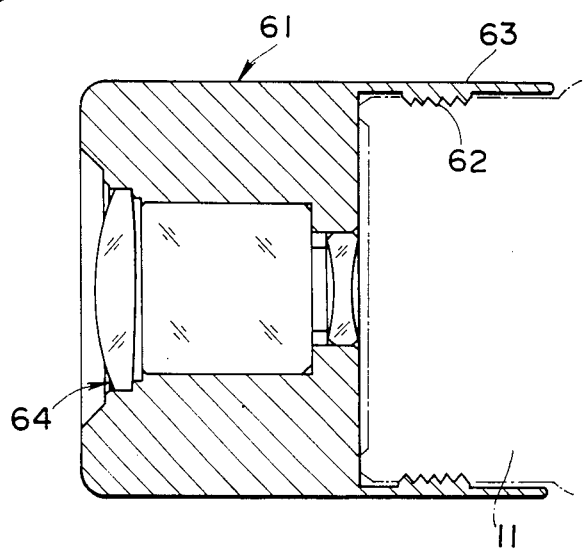

A visual field angle converting optical adapter 61 shown in FIGS. 7 and 8 is used to convert the visual field angle of the standard objective part 11. The adapter 61 can be fitted instead of the hood 54 to the screw part 53 of the front frame 39 of the standard objective part 11.

A connecting ring part 63 is formed with a female screw 62 which is screwed with the screw part 53. The connecting ring point 63 is formed on the rear side of the optical adapter 61 and can be fitted with the standard objective part 11, indicated by the one-point chain line. The visual field angle converting optical system 64 is secured in a through hole formed in the part opposed to the objective front lens of the standard objective part 11.

Figure 9:
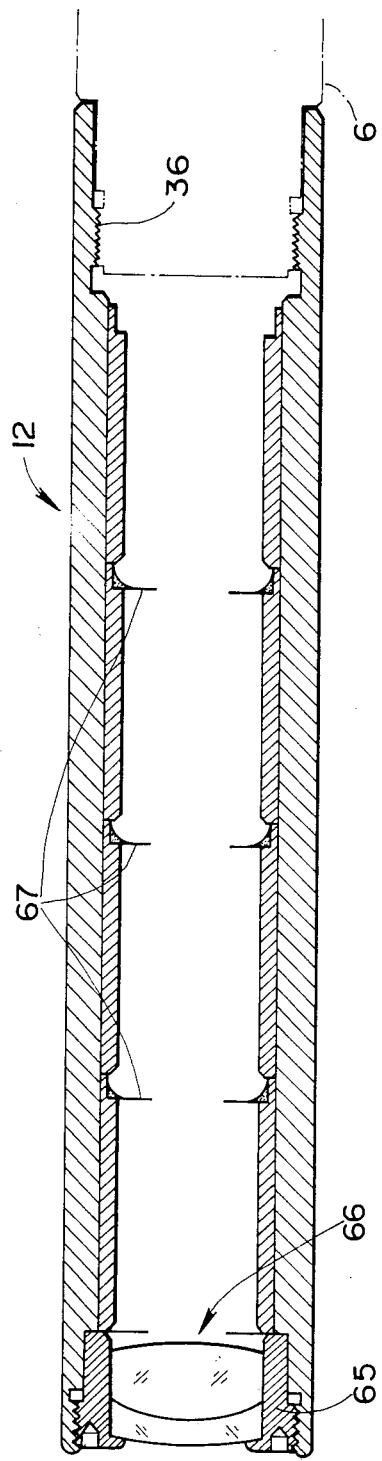
Figure 10:
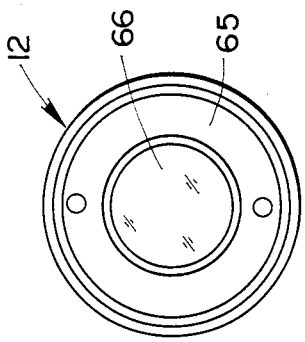

On the other hand, the tip 6 can be fitted with the high magnification objective part 12 shown in FIGS. 9 and 10 without being fitted with the standard objective part 11.

The high magnification objective part 12 can be fitted by screwing a female screw part 36, on its rear side, to the male screw part 35 formed on the outer periphery toward the front end of the front mouthpiece part 21 of the tip 6. The high magnification objective part 12 is to be screwed and is easily removably fitted by the rotating operation.

An objective optical system 66, forming images at a high magnification through a lens frame 65, is secured inside the front end of the tube body of the high magnification objective part 12. A plurality of flare stops 67 are fitted at proper intervals inside the tube body forming a light path. An image is formed at the front end of the image guide 9 through the objective optical system 66.

The image guide 9 is assembled on the front end side with the two bodies consisting of the image guide receiver 28 and the image guide holder 29. If the two bodies were made integral to be one body on the front end side of the image guide 9, the image guide would become so large in diameter on the front end side that it would be difficult to assemble from the eyepiece side. For example, since only the image guide receiver 28 is secured to the mouthpiece 31, the image guide 9 can be made so small in diameter at the front end as to be able to be passed from the eyepiece side. Thus, after the image guide is adjusted and fixed on the eyepiece side, the image guide holder 29 is screwed in from the front. The image guide holder 29 is then set in a position in which its front end surface contacts the front end surface of the image guide receiver 28 and is then fixed with the respective screws 27 so as to be able to be easily assembled.

According to the thus formed embodiment, the standard objective part 11, in which the focus can be adjusted by the rotating operation of the focus ring 44, can be fitted non-rotatably (without rotating) by fitting the ring part 23, which is its connecting part to the front mouthpiece part 21, and then securing it with the respective screws 26. Therefore, even if the focus is adjusted, the connecting part will not loosen.

On the other hand, there is an advantage that, for example, the high magnification objective part 12, which has a fixed focus and which requires no focus adjustment by the rotating operation, can be easily removably fitted by screwing it to the male screw part 35 which is formed on the front mouthpiece part 21. Thus, the high magnification objective part 12 becomes a rotary connecting part.

Thus, there are formed selective connecting means whereby the objective part, in which the focus is adjustable by the rotating operation, is non-rotatably connected. Also, the objective part of a fixed focus, in which the focus is not adjusted, is connected by the rotating operation. Therefore, the connection can be used with any desired objective part which is to be connected and the disadvantages of the prior art example are eliminated.

As evident from the above explanation, the objective part to be fitted to the male screw part 35 in the tip 6 of the embodiment is not limited to the high magnification objective part 12.

Inside the tip of the embodiment, the image guide 9 is provided but the light guide may also be provided. In such a case, the light guide may be formed, for example, to be a concentric ring.

In the illustrated endoscope, a curvable part is not shown to be formed but may be formed.

It is apparent that a wide range of different working modes can be formed without departing from the spirit and scope of the present invention. The present invention is not restricted by a specific working mode except being limited by the appended claims.

What is claimed is:

1. An objective part replaceable endoscope tip comprising:
    either one of
        a first kind of objective part having an objective optical system provided with a rotary adjustment mechanism by a rotating operation, and
        a second kind of objective part having an objective optical system having no rotary adjusting mechanism; and
    an insertable part of the endoscope having a tip;
    an image transmitting means being inserted through said insertable part;
    a non-rotary fitting part being in said tip, said non-rotary fitting part being for said first kind of objective part; and
    a rotary fitting part being in said tip, said rotary fitting part being for said second kind of objective part.

2. An objective part replaceable endoscope tip according to claim 1 wherein said rotary adjusting mchanism of the first kind of objective part forms a focus adjusting mechanism.

3. An objective part replaceable endoscope tip according to claim 2 wherein said focus adjusting mechanism of the first kind of objective part being moved in the optical axial direction by a sliding ring fitted with a part of said objective optical system through a cam pin by rotation of a rotatable ring.

4. An objective part replaceable endoscope tip according to claim 1 wherein said first kind of objective part forms a fitting part fittable with a hood at the front end.

5. An objective part replaceable endoscope tip according to claim 1 wherein said first kind of objective part is fittable with a visual field angle converting optical adapter at a front end.

6. An objective part replaceable endoscope tip according to claim 1 wherein said rotary fitting part is a screw part screwed to a screw of said second kind of objective part.

7. An objective part replaceable endoscope tip according to claim 1 wherein said non-rotary fitting part is formed of a mouthpiece fitting a ring part at a rear end of said first kind of objective part and a fixing means from the side of the fitting part.

8. An objective part replaceable endoscope tip according to claim 7 wherein said rotary fitting part is formed of a screw part made somewhat small in the diameter on a front end side of said mouthpiece part.

9. An objective part replaceable endoscope tip according to claim 1 wherein a flexible fiber bundle forming said image transmitting means is fixed on a front end side with a ring-shaped holding member fitted between a ring-shaped receiving member fixed on an outer periphery of said front end and having a screw part formed on the other periphery and a mouthpiece part forming said non-rotary fitting part and a fixing screw means from a side.

10. An objective part replaceable endoscope tip according to claim 9 wherein said ring-shaped holding member is expanded in diameter on the front side so as to be fittable from the front side.

11. An objective part replaceable endoscope tip according to claim 8 wherein said mouthpiece part forms a fitting part fitting the small diameter part of the ring part at a rear end of said first kind of objective part on the front side of said screw part.

* * * * *